US012702460B2

(12) United States Patent
Roesler

(10) Patent No.: US 12,702,460 B2
(45) Date of Patent: Aug. 11, 2026

(54) RESILIENTLY EXPANDABLE STERILIZABLE BULK PACKAGING

(71) Applicant: Roesler IP GmbH, Hergensweiler (DE)

(72) Inventor: Thiemo Roesler, Wangen/Neuravensburg (DE)

(73) Assignee: Roesler IP GmbH, Hergensweiler (DE)

( * ) Notice: Subject to any disclaimer, the term of this patent is extended or adjusted under 35 U.S.C. 154(b) by 0 days.

(21) Appl. No.: 18/882,172

(22) Filed: Sep. 11, 2024

(65) Prior Publication Data

US 2025/0090210 A1 Mar. 20, 2025

(30) Foreign Application Priority Data

Sep. 18, 2023 (EP) .................................... 23198030

(51) Int. Cl.
*B65D 33/16* (2006.01)
*A61B 17/86* (2006.01)
*B65D 85/24* (2006.01)

(52) U.S. Cl.
CPC ............ *A61B 17/865* (2013.01); *B65D 33/16* (2013.01); *B65D 85/24* (2013.01); *B65D 2255/00* (2013.01)

(58) Field of Classification Search
CPC ...... A61B 17/865; B65D 33/16; B65D 85/24; B65D 2255/00
USPC ........... 383/92, 95, 61.1; 422/547, 555, 560; 206/363, 370
See application file for complete search history.

(56) References Cited

U.S. PATENT DOCUMENTS 2,547,097 A * 4/1951 Schjeldahl ............. B65D 33/16 206/274
3,455,359 A * 7/1969 Schweizer ............. A45C 13/06 150/123
4,765,381 A * 8/1988 Castle ...................... A45C 3/00 383/97
4,892,525 A 1/1990 Hermann et al.
5,628,966 A * 5/1997 Corby ....................... A61L 2/26 422/26
8,261,953 B2 * 9/2012 McSavaney ............. B65D 1/32 222/491
8,641,278 B2 * 2/2014 Ducauchuis ....... A44B 18/0069 24/410
2003/0215160 A1 * 11/2003 Kohl .................... B65D 33/007 383/33

(Continued)

FOREIGN PATENT DOCUMENTS

DE 202014100438 U1 4/2014
DE 102013019452 A1 5/2015

OTHER PUBLICATIONS

European Patent Office, "Search Report," for European Patent Application No. 23198030.1, Jan. 16, 2024 (German only).

*Primary Examiner* — Jacob K Ackun
(74) *Attorney, Agent, or Firm* — Dentons Cohen & Grigsby, P.C.; Michael E. Dukes

(57) ABSTRACT

Resilient expandable packaging (1, 20) for small-part items (17) in the medical field, consisting of a packaging body (1, 20) open on one side with a packaging space (25, 25') closed at the bottom, which merges into a resiliently expandable closure part (6) on its upper side, wherein in the transition region between the closure part (6) and the packaging space (25, 25') one or more locking knobs (11, 12) are arranged, which form a resiliently expandable closure gap (13, 13') therebetween.

16 Claims, 10 Drawing Sheets

(56) References Cited

U.S. PATENT DOCUMENTS

| | | | | |
|---|---|---|---|---|
| 2007/0092398 | A1* | 4/2007 | McDonald | A61L 2/206 206/439 |
| 2010/0172794 | A1* | 7/2010 | Ferlic | A61M 39/16 422/294 |
| 2014/0072247 | A1* | 3/2014 | McDonough | B65D 33/243 383/65 |
| 2015/0083627 | A1* | 3/2015 | Gorman | B65D 75/004 206/439 |
| 2017/0095308 | A1 | 4/2017 | Roesler et al. | |

* cited by examiner

A-A

Squeeze

B
B

B-B
26
21
88

A
A
Squeeze
1
19
11,12
17

A-A
13
12
12
11
19
11
B
B 13
18
13
C
C 19
17'

B-B
17
25

C-C

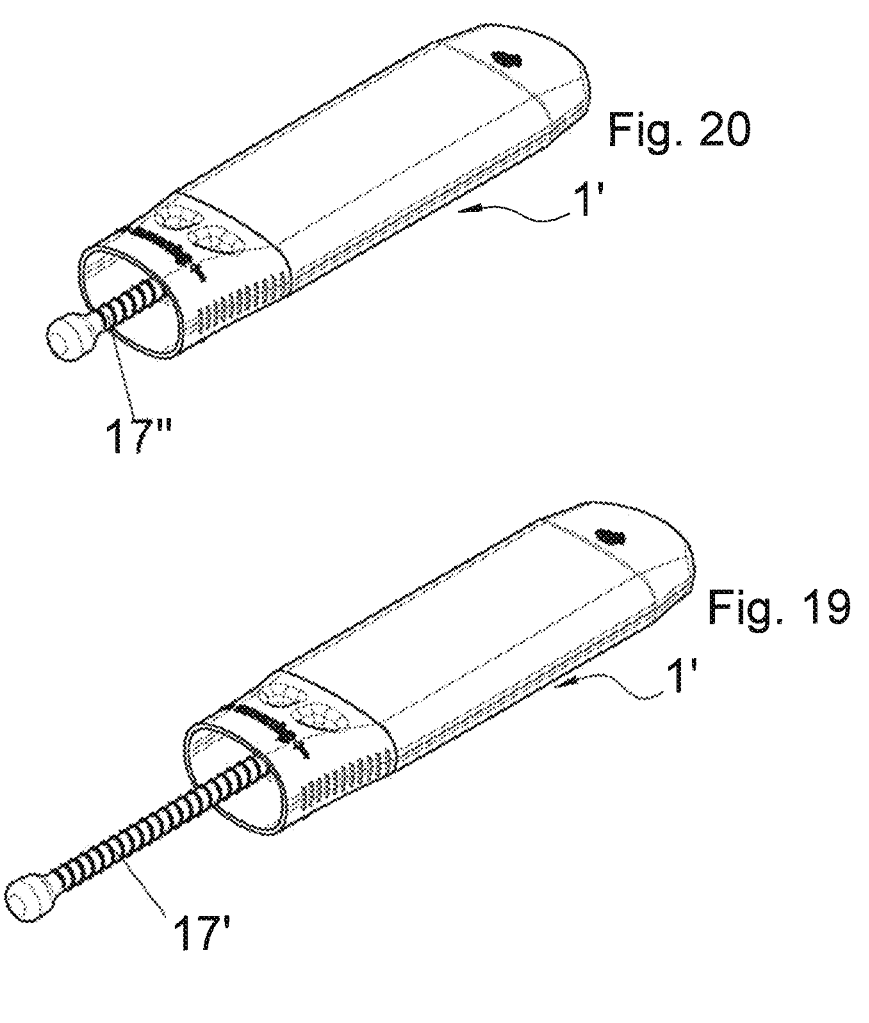
Fig. 20
1'
17"
Fig. 19
1'
17'
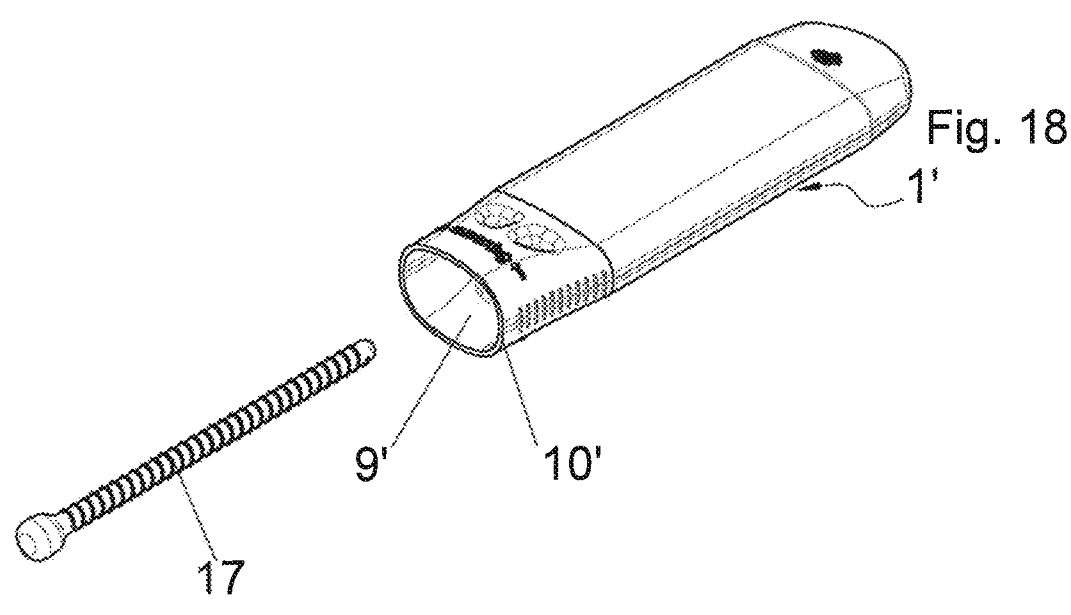
Fig. 18
1'
9'
10'
17

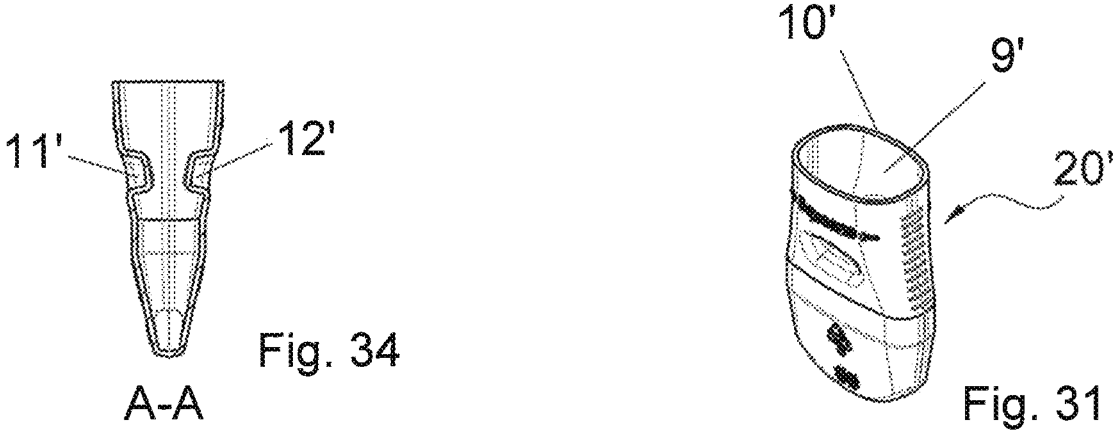
Fig. 34
Fig. 31
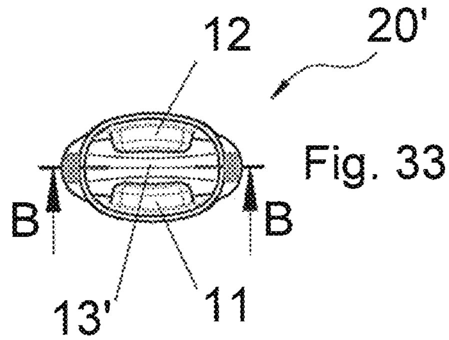
Fig. 33
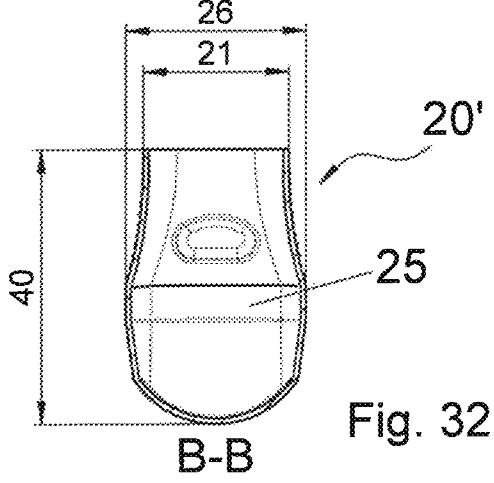
Fig. 32

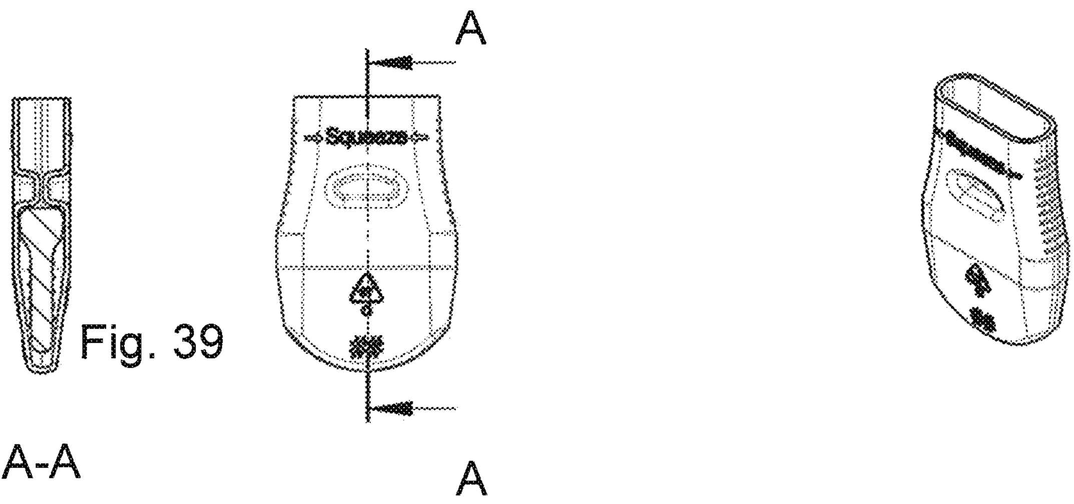
A
Squeeze
Fig. 39
A-A
A
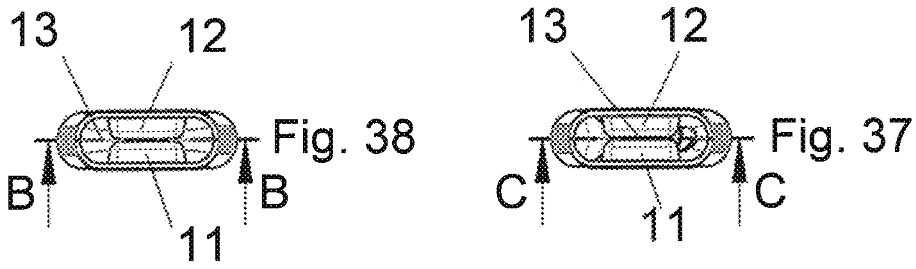
13
12
Fig. 38
B
B
11
13
12
Fig. 37
C
C
11
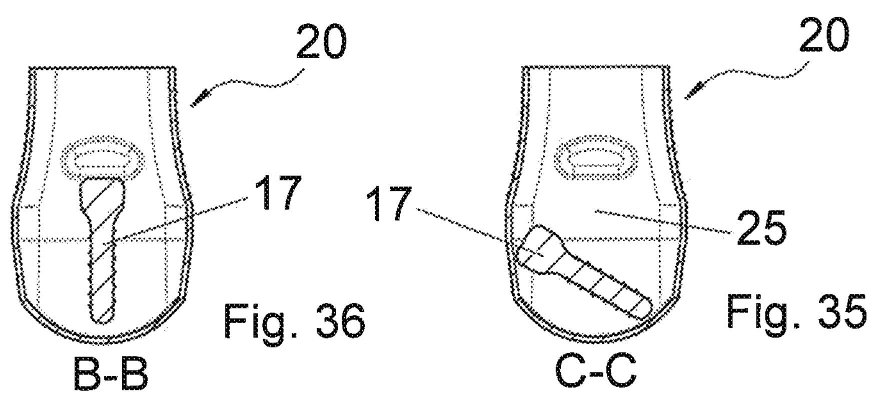
20
17
Fig. 36
B-B
20
17
25
Fig. 35
C-C

A-A

B-B

RESILIENTLY EXPANDABLE STERILIZABLE BULK PACKAGING

CROSS REFERENCE TO RELATED APPLICATION

This application claims priority to European Application No. 23198030.1, filed Sep. 18, 2023, the entire contents of which is incorporated herein by reference.

TECHNICAL FIELD

The subject matter of the invention is a resiliently expandable, sterilizable packaging for small-part items from the medical field in accordance with the preamble of claim 1.

SUMMARY

The resiliently expandable packaging serves as packaging for sterile medical small parts and spare parts, which are used in particular in surgery, orthopedics, and other medical fields. Such items must be able to be removed from their packaging during the operation-preferably with one hand-easily, without disruption, and while maintaining sterility.

The purpose of a packaging according to the prior art and the present invention is to provide a sterilizable packaging for small-part items of any kind from the medical field, which can preferably be sterilized by radiation.

From DE 10 2013 019 452 B4, a resiliently expandable individual packaging for elongated items has become known, wherein the item consists of at least one head of enlarged diameter and an adjoining bolt part of reduced diameter. The individual packaging is formed from an approximately cylindrical packaging sleeve which is open at least on one side at the front and which consists of a resiliently bendable material and which has at least one upper insertion opening for inserting or removing the elongated item, whereby only the head of the item to be held is held in a position-secured manner in the region of the insertion opening of the packaging.

A disadvantage is that the known individual packaging is dependent on holding the head of an elongated item—e.g., a screw—which severely limits the field of application. Other items that do not have such a head with an enlarged diameter cannot be held in a position-secured manner.

Another disadvantage of the known individual packaging is that the individual packaging has to be individually adapted to the diameter of the screw head, which means that a large number of individual packages have to be produced that are adapted to different screw shapes and screw lengths as well as head diameters.

There is only a small grip region, which is only present in the region of the expandable neck of the individual packaging, which means that the gripping surfaces are small and therefore difficult to operate.

Since the screw head of the screw to be held is located in the region of the insertion opening, there is a risk that an operator in the sterile surroundings of the operating room may inadvertently touch the screw head and thus contaminate it, which can result in serious surgical damage.

With the known individual packaging, there was therefore an increased risk of contamination because the screw head was accessible from the upper insertion opening, which should be avoided.

With the known individual packaging, only a single elongated item can be packaged at a time, assuming that a screw head or a head with an enlarged diameter is present, because the holding function takes place in this region. It was therefore only a roughly linear, resiliently expandable clamping collar that carried out the holding function. The operation of this clamping collar was inconvenient due to a lack of sufficient gripping surfaces.

Furthermore, the well-known individual packaging depends on a specific head shape being specified, otherwise the packaging will not work. Therefore, even with the well-known individual packaging, only a single item can be packaged at a time and not a plurality of pourable items at the same time, which should be protected as far as possible from contact.

The invention is therefore based on the object of developing a packaging for pourable items of the type mentioned at the outset in such a way that the items to be packaged can be safely placed in a resiliently expandable packaging and that these items are protected against unintentional contact.

To achieve the object, the invention is characterized by the technical teaching of the independent claim.

It is preferred if one or more locking knobs are arranged in the transition region between the closure part and the packaging space, which locking knobs form a resiliently expandable closure gap therebetween.

It is therefore a flat packaging bag into whose packaging space one or more items are poured and which can be removed by pressing the gripping surfaces by finger pressure through the closure gap which then opens.

Removal can be achieved by turning the bulk packaging upside down and then opening the closure gap by pressing the gripping surfaces by finger pressure, after which one or more items fall out due to gravity.

In another variant, the item can be removed from the packaging space using a magnetic tool or a gripping tool when the packaging is upright and the closure gap is open.

The arrangement of locking knobs, which limit the packaging space at the top and form the closure gap, has the advantage that in the event of incorrect operation, for example if the medical assistant holds the packaging upside down and wants to empty it, the items stored in the packaging space are prevented from accidentally falling out. The locking knobs, which can only be activated by finger pressure and form the closure gap, are a safety device against accidental emptying.

It is preferred if there is a resiliently expandable, flat packaging body overall, the upper closure part of which is resiliently expandable, wherein the closure part is formed by at least two gripping ribs arranged opposite one another on the narrow sides of the packaging body, which can be resiliently pressed against one another, whereby the closure gap arranged in the lower region of the closure part and formed by one or more locking knobs widens.

The widened closure gap allows the items poured into the packaging space to be removed from the packaging if the packaging is facing downwards with the removal opening.

It is preferred if the one or more locking knobs are arranged on the inner side of the front wall and the rear wall of the closure part, facing each other and aligned with each other, whereby they move away from each other when suitable deformation pressure is applied to the opposing gripping surfaces and thereby form an open closure gap through which the item can be inserted or removed.

According to the invention, it is therefore preferred if the upper closure part of the packaging body is delimited by an opening that can be widened by finger force, and that beyond this opening one or more opposing locking knobs are arranged in alignment on the front and rear walls, which form an expandable closure gap between them.

The technical teaching provided has the advantage that the items to be packaged no longer necessarily have to be a screw with a screw head with an enlarged diameter, but they can be items of any shape which can also be poured through the opening of the packaging widened in the upper region and through the widened closure gap underneath into the lower packaging space of the packaging body without there being a risk of contact in the upper region of the opening of the packaging body.

This makes it possible to meet improved sterile requirements and to securely package one or more items in such a packaging body, which can be packaged in the packaging region in a way that is safe from contact when the closure gap is closed, without the need for a single item to be held in a position-secured manner.

Here, the invention differs from the prior art according to DE10 2013 019 452 B4, because the known packaging was only designed to hold a single screw and the shape of the packaging had to be adapted to the shape of the item to be held. With the invention, this is no longer necessary. This also eliminates the need to provide a large number of packaging variants for a large number of different items to be packaged, because a large number of—even different—items can be packaged in a single package, which can be, for example, pins, screws, nuts, plates, or other packaging items that, when the opening of the packaging is widened, fit through the expandable closure gap arranged at a distance below the packaging mouth and can no longer leave the packaging when the closure gap is closed.

The locking force for the locking knobs forming the closure gap is defined by the resilient restoring force of the plastics material in the neck region of the packaging.

In another embodiment of the invention, it can additionally be provided that the locking force (closing force) of the closure gap is enlarged by the locking knobs forming a toothed engagement.

Because the technical teaching of the invention makes it possible for the first time to form a protected packaging space in the bulk packaging in which one or more items can be safely stored, there is the further advantage that in the upper region, i.e., beyond the locking knobs and therefore in the region of the upper edge, it is now possible for the first time to securely close the entire opening by means of a closure means.

A first secure closure of the opening edge is, for example, that the plastics material from which the packaging body is made can be welded by means of welding in order to create an absolutely tight packaging, which was not possible with the known individual packaging according to the prior art.

Another closure option is, for example, that the opening of the packaging body in the upper region of the peripheral edge can be closed with a sealed and tear-off closure sheet or with a closure adhesive.

In any case, it is important in the invention that a protected packaging space is formed beyond and below the locking knobs and that the region of the packaging body located above the locking knobs can be sealed in any desired manner, with an airtight seal, for example by welding, being particularly preferred.

Since it is a packaging for sterilizable items, such packaging bodies are preferably used in the medical field and the items to be packaged are preferably medical, sterilizable items, such as screws, knobs, nuts and pins, and the like. Sterilization is preferably carried out on the packaging filled with packaging items and tightly sealed by means of radiation sterilization.

In another preferred embodiment, it is provided that the resiliently expandable bulk packaging is placed in an airtight bag packaging and then sterilized.

The packaging body should be easy to handle. It should preferably be operated with the fingers of one hand. Therefore, the preferred dimensions of the packaging are in the range of a length of, for example, 40 mm up to a length of 400 mm. A preferred width is about 26 mm up to a preferred width of about 200 mm.

These are merely preferred dimensions which do not limit the scope of the invention.

A further characteristic of the packaging according to the invention is that it is a resiliently deformable flat body made of plastics material, preferably transparent—or also slightly colored—i.e., a body which consists of two walls parallel to one another, namely a rear wall and a front wall, and the two walls are parallel to one another and are laterally connected by narrower side walls, whereby an overall approximately flat body with an approximately rectangular cross section is formed.

A preferred shape of the packaging body is a rectangular shape or a shape approximating to a rectangular shape with rounded corners.

Another design provides that the parallel front and rear walls have a slightly bulbous (convex) shape.

The rectangular shape has the advantage that the packaging is protected against accidentally rolling away from a storage surface.

The device is operated by finger pressure on opposing gripping ribs, which are arranged in the region of the upper closure part. The actuation force corresponds approximately to the finger force required to open a clothespin.

The approximately flat, oval cross-sectional shape of the packaging body is converted into an approximately round shape in the neck region. As a result, the previously oval opening in the upper region of the closure part widens and the locking knobs arranged in the lower region of the closure part, which are aligned with one another and form the closure gap therebetween, move away from one another, whereby the closure gap opens and one or more items can be removed or inserted from the lower packaging space through the opened closure gap.

For larger packaging bodies, it is provided that locking knobs are arranged in pairs on both the front and rear walls, each opposite one another. This means that the locking knobs are arranged in pairs on the front wall and in pairs on the rear wall and are aligned in a horizontal line to one another and form the closure gap that is expandable by finger pressure or—in the case of very large packaging—by machine pressure.

The packaging body is preferably designed to be resilient in its upper neck region so that the gripping ribs can be pressed against one another by finger pressure in order to widen the peripheral opening edge.

The invention is not limited to this. In another embodiment, in the case of larger packaging, it may be provided that machine assistance is also used for resilient deformation of the neck region for filling or removing packaging items.

However, for smaller packaging bodies it is sufficient to arrange only one pair of opposing locking knobs in the lower part of the neck region. Therefore, only one locking knob is provided on each side of the packaging. In the case of larger packaging, a plurality of locking knobs can be arranged at a distance from one another on each side of the package, which are in gap engagement with the locking knobs arranged on the opposite side of the package to form the closure gap.

The shape of the locking knobs can be varied within wide limits. It can be provided that the locking knobs safely limit the closure gap in the closed position, but on the other hand do not prevent the packaged item from being shaken out or slipping out. Therefore, the locking knobs in the gap engagement can be spaced apart from one another. In this variant, there is therefore no frictional mutual contact between the locking knobs.

In another variant, the locking knobs in the gap engagement can have a mutual frictional contact.

It is also preferred if the locking knobs arranged in pairs form a mutual distance between themselves, because when such a packaging body is compressed, the material between the locking knobs bends in the region of this intermediate distance and thus an improved widening of the opening and the closure gap is possible.

In another embodiment of the invention, it can be provided that the locking knobs arranged in pairs on the front wall and the rear wall are connected to one another, i.e., the central distance between the locking knobs—which previously formed the kink region—is then eliminated. This ensures that the two locking knobs arranged in pairs merge into a single horizontal elongated locking knob on the front wall and the rear wall, whereby it is always assumed that the locking knobs on the front and rear walls are aligned with one another.

Furthermore, the invention does not depend on the locking knobs being arranged on both the front wall and the rear wall. In a different embodiment, it can be provided that either only on the inner side of the front wall or only on the inner side of the rear wall there are individual locking knobs or locking knobs arranged in pairs, which form a closure gap to the smooth inner side of the opposite wall, whereby the closure gap is then no longer arranged centrally in the packaging body, but is offset laterally.

In a further embodiment of the invention, it is provided that the locking knobs arranged opposite one another on the front wall and the rear wall are not aligned with one another, but are laterally offset from one another on a horizontal line so that they form an interlocking row of teeth.

The locking knobs arranged at a distance on the front wall then engage in the gaps between the locking knobs arranged on the rear wall in the manner of a toothed engagement and thus form a toothed, labyrinth-like closure gap, which therefore has a special closure characteristic. In a first embodiment, the toothed engagement can allow mutual play between the interlocking locking knobs. In a second embodiment, the toothed engagement can also be frictional, i.e. the interlocking "teeth" of the locking knobs form an additional locking force, the amount of which exceeds the resilient restoring force of the plastics material in the neck region.

The locking knobs, which are directed against one another in pairs and form a mutual toothed engagement, do not only have to be present in pairs, but in another variant of the invention it is sufficient that one locking knob is arranged on the front side and an opposite locking knob is arranged on the rear side and the two locking knobs are not aligned with one another but are offset laterally from one another in order to also allow for a toothed engagement and thus form a bent closure gap.

Thus, while the first embodiments, which are preferably described in the drawings, describe a horizontal, straight continuous closure gap, in the variants just described the locking knobs are arranged in such a way that they form a mutual toothed engagement so as not to form an elongated, flat closure gap, but a serrated, interlocking closure gap.

The subject matter of the present invention results not only from the subject matter of the individual claims, but also from the combination of the individual claims with one another.

All information and features disclosed in the documents, including the abstract, in particular the spatial configuration shown in the drawings, could be claimed as substantial to the invention insofar as they are new compared to the prior art, individually or in combination. The use of the terms "substantial" or "according to the invention" or "substantial to the invention" is subjective and does not imply that the features so named must necessarily be part of one or more claims.

In the following, the invention is explained in more detail with reference to drawings which merely illustrate one embodiment. Further substantial features and advantages of the invention will become apparent from the drawings and their description.

BRIEF DESCRIPTION OF THE DRAWINGS

In the drawings:

FIG. 18 is a representation of the opened packaging body when inserting a packaging item into a first position;

FIG. 19 is the same representation as FIG. 18 in a second packaging position;

FIG. 20 is the same representation in a third packaging position;

FIG. 31 is the representation of the packaging body according to FIG. 26-FIG. 30 in the widened state;

FIG. 32 is a longitudinal section of the packaging body according to FIG. 31;

FIG. 33 is a top view of the packaging body;

FIG. 34 is the section along a line A-A in one of the previous drawings;

FIG. 35 is the packaging body according to FIGS. 26-34 with another packaging item;

FIG. 36 is a different packaging situation compared to FIG. 35;

FIG. 37 and FIG. 38 are the top view of the representations in FIGS. 35 and 36;

FIG. 39 is the section along one of the lines A-A in the previous drawings;

DETAILED DESCRIPTION

Figures 1, 2, 3, 4, 5, 6:
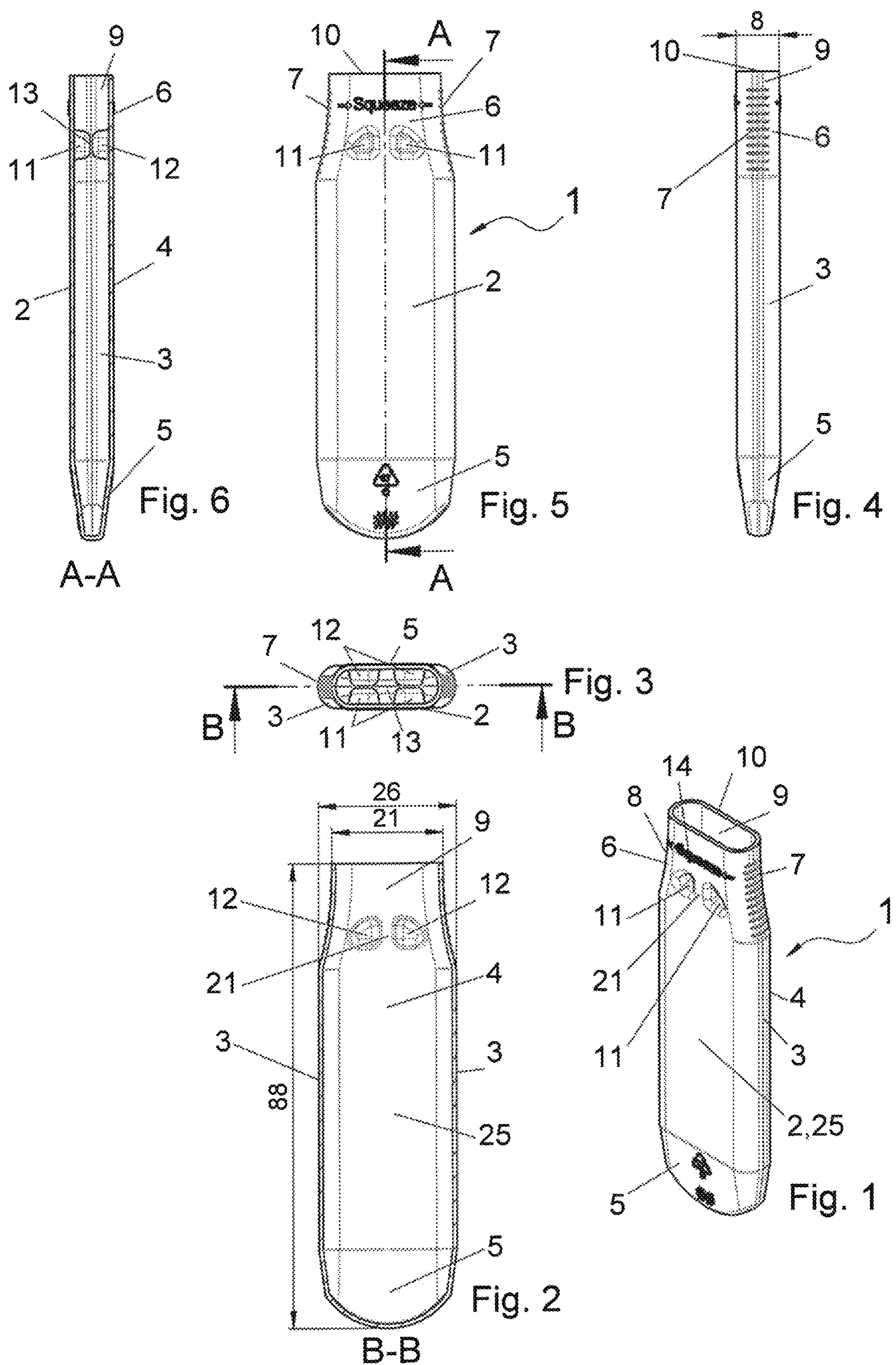
FIG. 1 is a perspective view of a first embodiment of a packaging body.
FIG. 2 is a longitudinal section through the packaging body along the section line B-B in FIG. 3.
FIG. 3 is a top view of the packaging body from the direction of its opening.
FIG. 4 is a side view of the packaging body according to FIGS. 1 and 2.
FIG. 5 is the front view of the packaging body.
FIG. 6 is a section along line A-A in FIG. 5.

The packaging body 1 according to the invention has a substantially flat, elongated body shape, i.e., it is approximately rectangular in cross section, since it consists of a flat front wall 2, a parallel rear wall 4 and two side walls 3 which adjoin one another in one piece.

The entire packaging body 1 is manufactured in one piece using the blow molding process and consists of a resilient plastics material, preferably a TPU plastics material. Therefore, it is sterilizable, weldable, and abrasion-resistant. It is preferably transparent or lightly colored and permanently resilient. It forms a flat packaging bag. It preferably has a hardness in the range of 45 to 95 shore-A and particularly preferably a hardness of 85 shore-A+−5.

The preferred dimensions have already been mentioned in the general description part, whereby the packaging body according to the invention is intended to be suitable for the packaging of relatively small items, as they occur in the medical field, whereby the term "small items" also includes organ replacement parts, such as artificial knee joints, shoulder joints, bone nails, hip joints, bone saw blades and/or small parts, such as screws, nuts, pins, plates and the like.

The items described above are intended to describe only the largest packages in the packaging body. The embodiments shown in the drawings, however, show preferred actual dimensions of a packaging body in a 1:1 scale for the sterile packaging of screws, nuts, pins, plates, and the like. The packaging bodies shown in the drawings are therefore actually shown in natural size.

The packaging space 25 receiving the items is elongated and closed off at the bottom by a rounded bottom part 5. The packaging space 25 and the base part 5 are also resiliently compressible and can be resiliently deformed by finger pressure from their flat shape into a bulbous shape approximating a round shape.

This resilient deformability facilitates the removal of items 17 stored in the packaging space 25.

The transition from the oval packaging space 25 into the oval neck region 8 of a closure part 6 adjoining at the top is effected via an arched convex contour. The neck region 8 is therefore reduced in width in cross section compared to the packaging space 25. It forms an upper opening 9, which can be converted by resilient deformation into an opening 9' that approximates a round shape.

The undeformed oval opening 9 is defined by a peripheral edge 10 and in the region of the side walls 3, in the region of the closure part 6, opposite gripping ribs 7 are arranged in alignment with one another, which can be squeezed against one another by finger pressure or—in the case of automatic packaging machines—with the aid of a machine. The resulting shape is described in the following FIG. 7 et. seq.

It is important that a locking mechanism is arranged in the lower region of the closure part 6, which in the embodiment shown is formed from pairs of opposing locking knobs 11, 12 that are arranged in alignment with one another, with a pair of locking knobs 11 being arranged on the inner side of the front wall 2 and an identical pair of locking knobs 12 being arranged on the inner side of the rear wall 4, and the pairs of locking knobs 11, 12 being arranged in alignment with one another, as can be seen from FIG. 3. In the closed state, they therefore form a closure gap 13 running in a horizontal direction, which in the closed state can have a preferred width in the range of 0 mm to 1 mm.

In the general description it has already been pointed out that it is not necessary for the solution that the locking knobs 11, 12 arranged in pairs opposite one another touch one another. However, in another embodiment it can be provided that the locking knobs 11, 12 are offset from one another in order to form a toothed, sealed, or unsealed engagement with one another.

It has also already been mentioned in the general description that, instead of the arrangement of paired locking knobs 11, 12, individual locking knobs 11, 12 can also be provided. However, more than two locking knobs can be arranged on one inner side of the front wall or one inner side of the rear wall.

Accordingly, the number of locking knobs arranged on the front wall 2 and on the rear wall 4 is not limited. There may be more than two.

It is preferred if a label 14 is arranged in the region of the closure part 6, which indicates that the gripping ribs 7 can be compressed against one another by finger pressure in order to bring the packaging into an open state.

FIG. 2-6 show further details of the construction, whereby it can also be seen from FIG. 2 that there is a distance 21 between the locking knobs 11, 12 arranged in pairs. The arrangement of the distance 21 allows for the material to bulge in the region of the distance 21 when the gripping ribs 7 are compressed against one another and to form a kink region, thus allowing for a reduction in the compression force when the closure part 6 is opened. This reduces the compression force caused by finger pressure and at the same time increases the width of the closure gap 15. In all cases, regardless of whether a bendable distance 21 is present or not, the compression force preferably corresponds to the force that must be applied to open a clothespin.

In another embodiment, it can be provided that the locking knobs 11, 12 arranged in pairs on the front and rear walls are each formed into a single horizontal locking knob.

When describing the present packaging body, it is irrelevant what shape the packaging items have, as shown below.

This means that the packaging items can have a length such that they just touch the underside of the locking knobs 11, 12 in the packaging frame 25 at the top and protrude into the bottom part 5 at the bottom. However, they can also be much shorter, so that the packaging has the characteristics of a pocket-shaped bulk packaging.

Thus, a large number of small and short items can be poured into the packaging space 25 via the opened closure gap 13' and then removed again when the closure gap 13' is opened.

FIGS. 7 to 12 show the opened packaging, assuming that mutual pressure is exerted on the gripping ribs 7 by finger pressure or with mechanical assistance in the directions of arrows 15, 16 and that the opening 9 is transformed into an approximately round-profile opening 9'. The closure gap 13 also opens because the locking knobs 11, 12 move away from one another and form an open closure gap 13'.

Figures 7, 8, 9, 10, 11, 12:
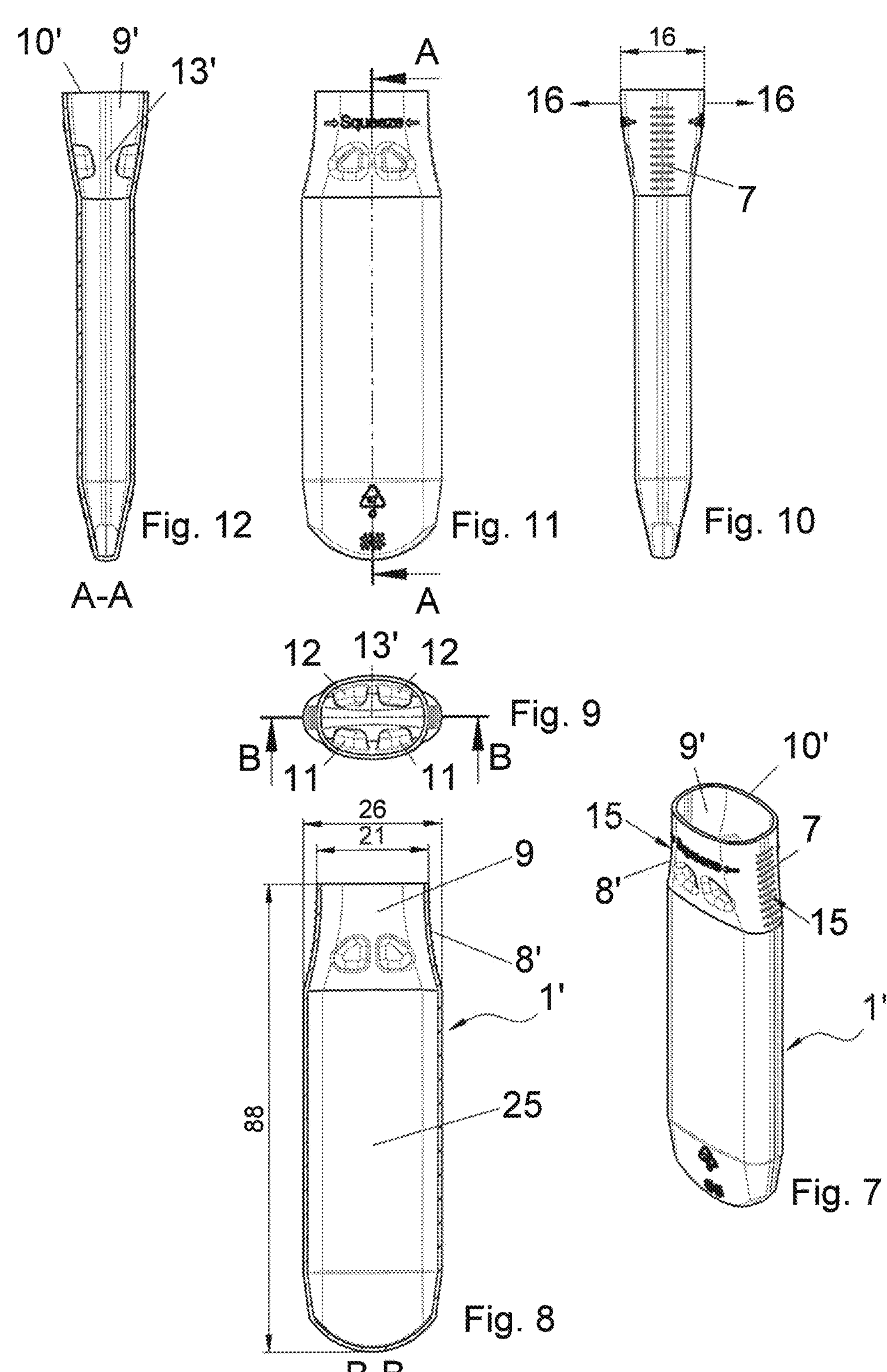
FIG. 7 is the perspective view of the packaging body in a widened state.
FIG. 8 is the longitudinal section through the packaging body.
FIG. 9 is the top view of the packaging body in the widened state.
FIG. 10 is the side view of the packaging body.
FIG. 11 is the front view of the packaging body.
FIG. 12 is a section along line A-A in FIG. 11.

According to FIG. 9, the items to be packaged can then be poured into the packaging space 25 through the opened closure gap 13'.

FIG. 12 shows that the locking knobs 11, 12 are profiled in a specific way, i.e., they have insertion bevels so that an item to be packaged can be inserted particularly easily via the insertion bevels.

Such insertion bevels or exit bevels arranged at the bottom can also be omitted.

FIGS. 13 to 17 show the packaging of a conformal item, i.e., an item 17 which substantially fills the packaging space 25.

Figures 13, 14, 15, 16, 17:
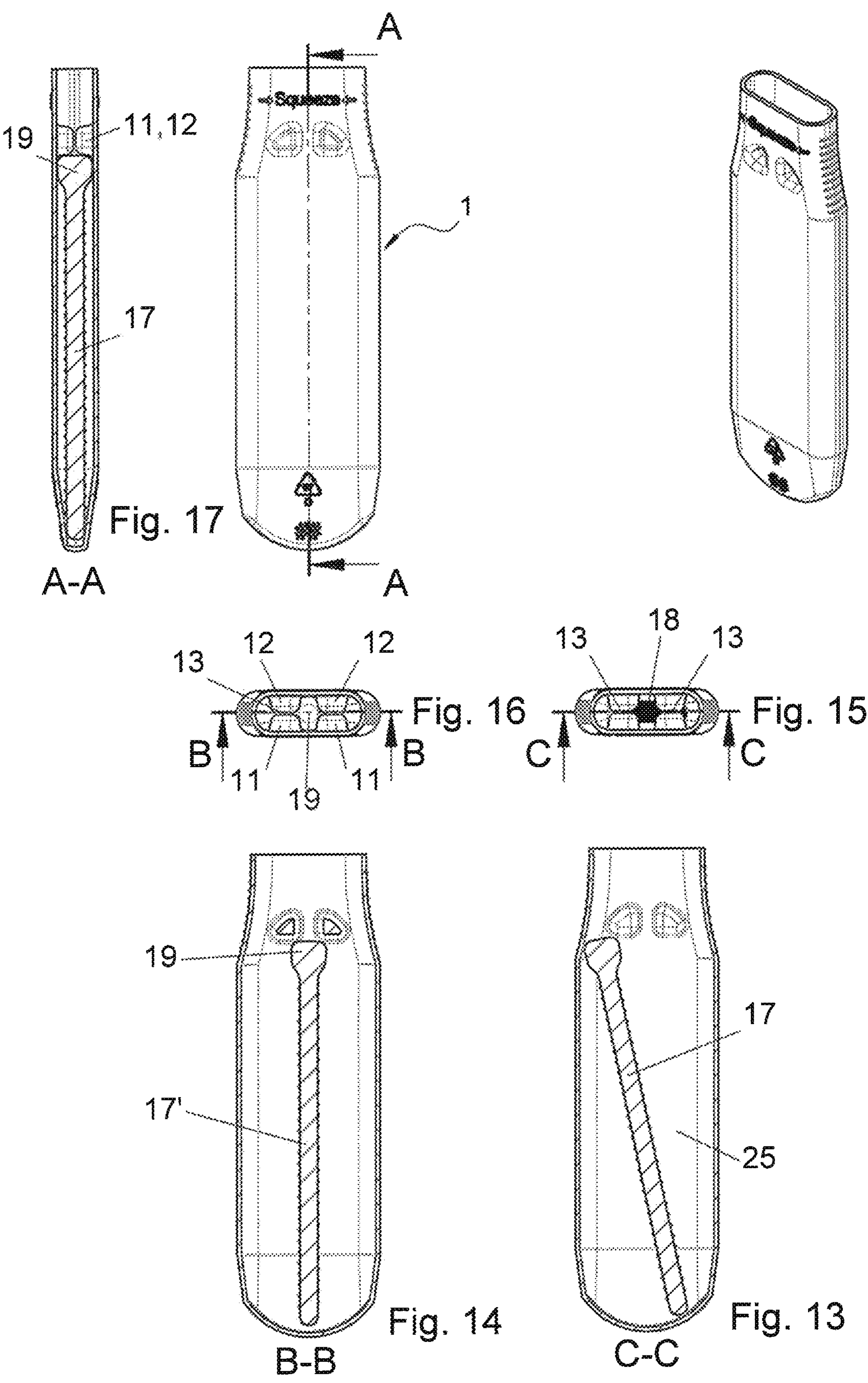
FIG. 13 is a section through the packaging body in the closed state with a packaging item.
FIG. 14 is the same representation as FIG. 13 with a packaging item in a different position.
FIG. 15 is a top view of the packaging body according to FIG. 13.
FIG. 16 is a top view of the packaging body according to FIG. 14.
FIG. 17 is a section through the packaging body along a line A-A according to the previous drawings with the packaging body inserted.

The item 17 can take an oblique position as shown in FIG. 13 or a straight position as shown in FIG. 14-. Its location in the packaging space 25 is therefore completely arbitrary. It is preferred if the packaging space 25 is also resiliently deformable by finger pressure.

It is therefore not necessary for the solution to bring the item 17 in a position-secured manner with its head against the underside of the locking knobs 11, 12, because it does not depend on this positional securing.

Figures 21, 22, 23, 24, 25:
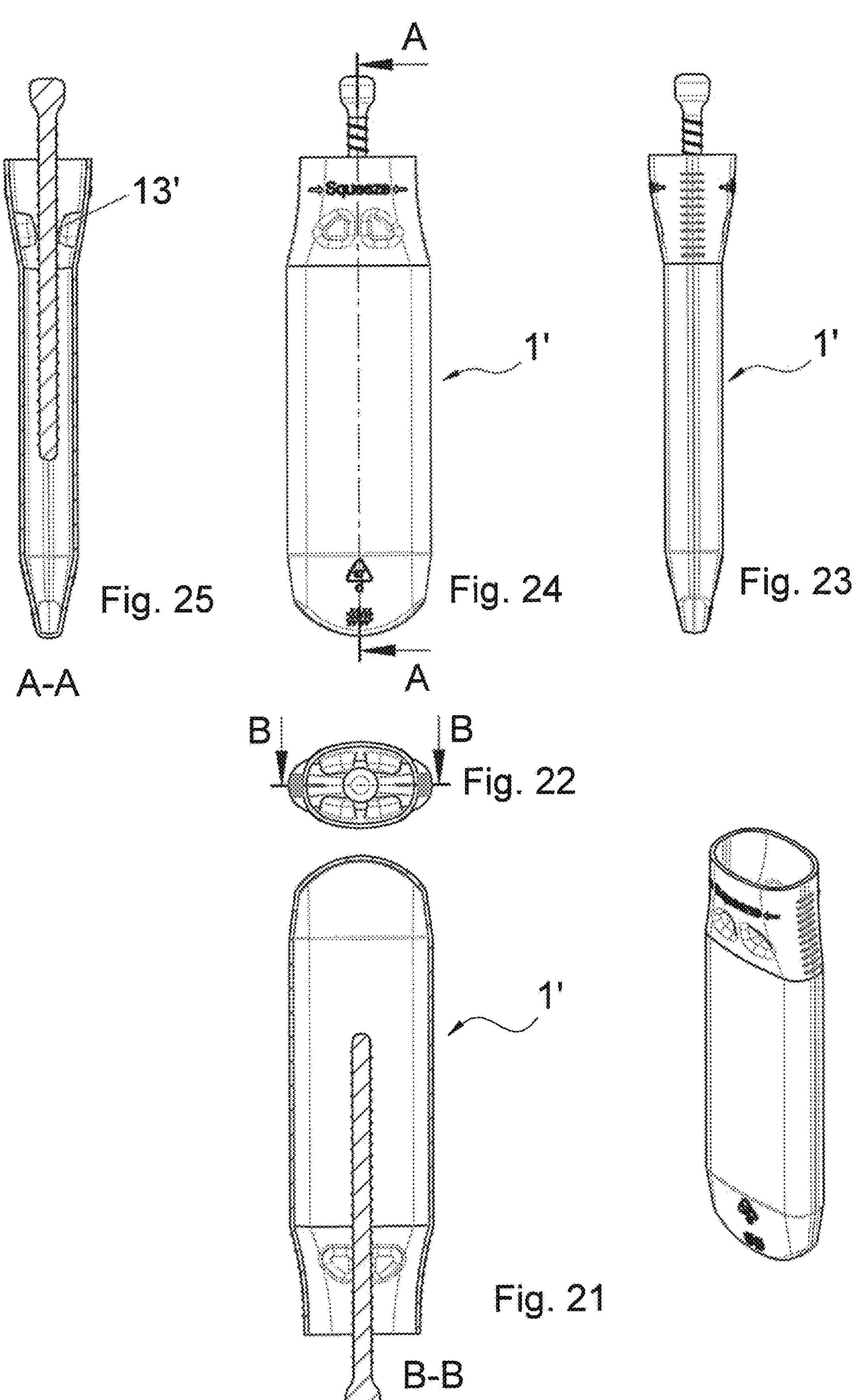
FIG. 21 is a representation of the section through the packaging as shown in FIG. 20.
FIG. 22 is the top view of the packaging body with the closure gap open and the packaging item inserted.
FIG. 23 is the side view of the widened packaging body.
FIG. 24 is the front view of the packaging body in the widened state.
FIG. 25 is a section through the packaging body along line A-A in FIG. 24.

FIGS. 21 to 25 show the packaging of such an item according to FIGS. 13 to 17, wherein FIGS. 18 to 20 show the step-by-step introduction of such an item 17, while FIG. 21 is a section through the packaging in the position of the item 17" according to FIG. 20.

FIG. 25 shows that the item is inserted with the closure gap 13' being open. The clear width of the closure gap 13' can be substantially larger than the diameter of the bolt of the item 17, so that the item falls freely into the packaging space 25.

FIGS. 26 to 30 show a further packaging body 20 which is reduced in its dimensions compared to the packaging body 1 and which has a shorter length, but here the dimensions of the opening 9 are substantially the same.

Figures 26, 27, 28, 29, 30:
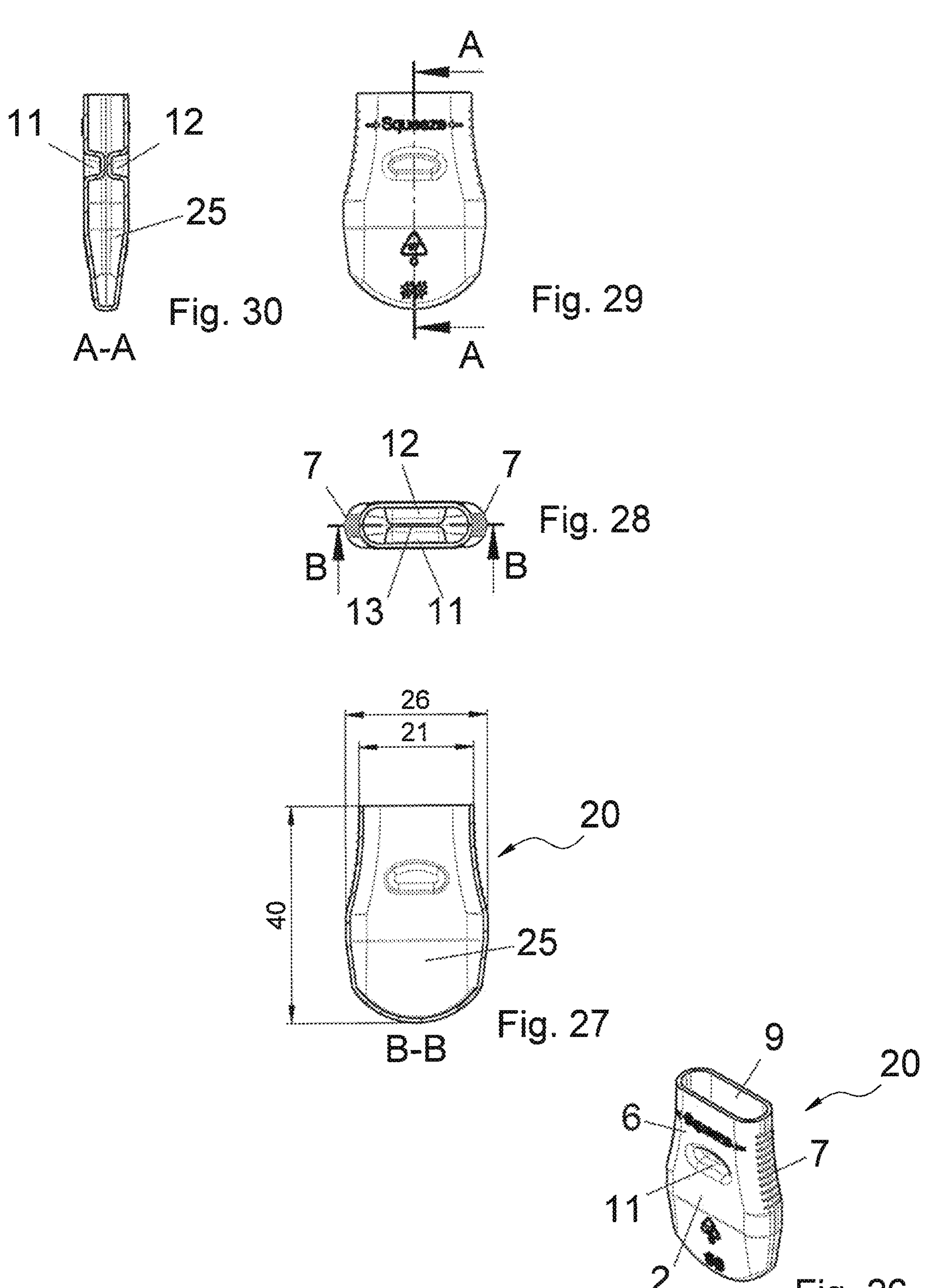
FIG. 26 is a second variant of a packaging body with smaller dimensions compared to the first variant.
FIG. 27 is the section through the packaging body.
FIG. 28 is the top view of the packaging body.
FIG. 29 is the front view of the packaging body.
FIG. 30 is a section along line A-A in FIG. 29.
Figure 42:
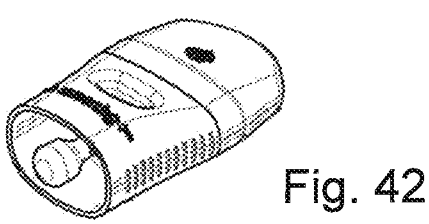
FIG. 42 shows a third position.
Figure 41:
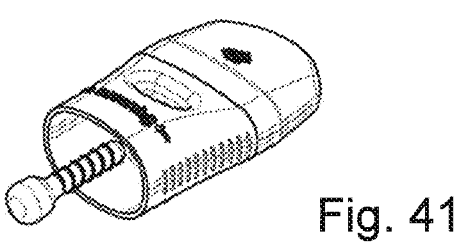
FIG. 41 shows a second position.
Figure 40:
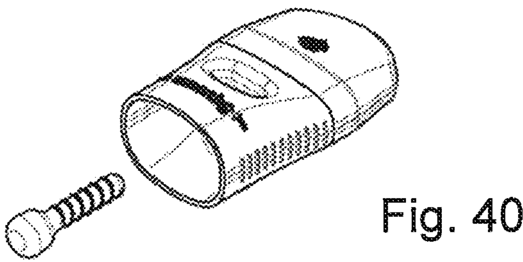
FIG. 40 is the packaging situation of the packaging container shortened in length in a first position.

Characteristic of these embodiments is that the resiliently expandable, sterilizable packaging bag has a shorter packaging length with a packaging space 25' with a reduced volume, and that in the closure part 6 there are no locking knobs 11, 12 directed against one another in pairs, but only a single locking knob 11 which is opposite a single locking knob 12, as can be seen for example from the section in FIG. 30.

Such a packaging body 20 can also be used as a closure plug of a sleeve-shaped packaging (not shown in detail), which is pressed into the packaging sleeve open on one side as a closure plug. The gripping surfaces then form friction-increasing projections that frictionally engage the inner sides in the region of the opening of the packaging sleeve.

The sleeve packaging consisting of these two parts can be used, for example, for the sterile packaging of saw blades for bone saws in medical technology. The sleeve packaging closed with the closure plug can be placed in an outer bag that tightly encloses the packaging and can be sterilized by radiation.

The shortened overall length results in a particularly simple packaging form of the packaging body 20, whereby here too it is not necessary for the locking knobs 11, 12 to be aligned opposite one another, but the locking knobs 11, 12 can also be arranged offset from one another in a horizontal line in order to allow for a distribution engagement.

Of course, it is also possible to form a packaging body 20 with reduced dimensions with locking knobs 11, 12 arranged in pairs, as described with reference to FIG. 1 et. seq.

Otherwise, the same reference signs apply to the same parts.

FIGS. 31 to 34 show the same packaging according to FIGS. 21 to 30 in the opened state, i.e., in the state in which the opening 9 has been widened and has been transformed into the opening 9' and the peripheral edge 10' in an approximately enlarged oval or round shape. As a result, the closure gap 13' has opened according to FIG. 33 and one or more packaging items 17 can be filled into the packaging space 25 located underneath through the opened closure gap 13'.

FIGS. 35 to 45 show the same packaging according to FIGS. 26 to 34 when receiving an item 17, wherein FIGS. 35 and 36 show that the item 17 can be located in any manner in the packaging space 25, and that several items can also be received in the packaging space 25 as bulk goods.

FIGS. 37 and 38 show the closed closure gap 13, wherein FIG. 39 shows a positionally correct arrangement of the item 17, which rests with its upper part on the underside of the locking knobs, to which the invention is not limited, however. The item can take up any position in the packaging space 25.

Figure 45:
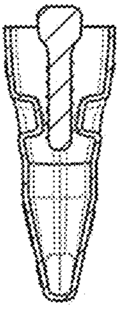
FIG. 45 is a sectional view when inserting a packaging item into the packaging body.
Figure 45:
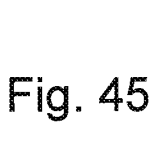
Figure 44:
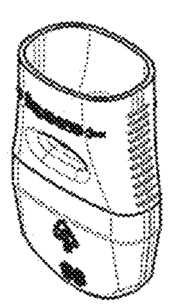
FIG. 44 is a top view of the opening.
Figure 44:
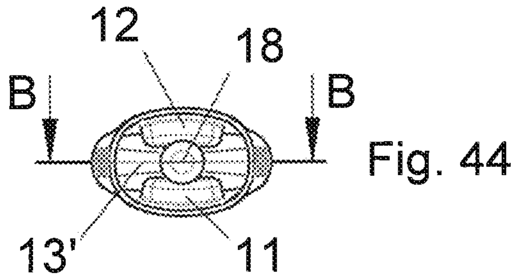
Figure 43:
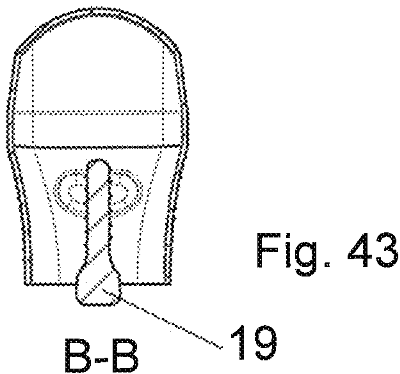
FIG. 43 is a section through the packaging body in the position shown in FIG. 42.

FIGS. 40 to 45 show the step-by-step insertion of such an item 17, whereby a passage channel 18 is formed between the locking knobs, through which the item 17 can be inserted according to FIG. 43 when the opposing locking knobs 11, 12 are opened and an enlarged closure gap 13' is present. This is also shown in FIG. 45.

The advantage of the present invention is therefore that there is a resiliently expandable, sterilizable pocket-shaped bulk packaging for one or more items, which can be closed at its front side and which can accommodate sterile items without the risk of contamination of these items through accidental contact, as was the case in the prior art.

In addition, it is possible to sterilize the item in the sealed packaging, which was not possible with the arrangement of the packaging body according to the prior art.

A particular advantage of the invention is also that the packaging body 1, 20 can be welded in the region of its opening 9 and is sterilizable with the item enclosed there in the packaging space 25 and remains sterile without the need for outer packaging.

LIST OF REFERENCE SIGNS

1) Packaging body
1') Packaging body
2) Front wall
3) Side wall
4) Rear wall
5) Base part

6) Closure part
7) Gripping rib
8) Neck region (of 6)
8') Neck region (of 6)
9) Opening v 9'
10) Edge
10') Edge
11) Locking knob (front)
12) Locking knob (rear)
13) Closure gap 13'
14) Labeling
15) Arrow direction
16) Arrow direction
17) Item, 17', 17"
18) Passage channel
19) Screw head
20) Packaging body
20') Packaging body
21) Distance
25) Packaging space
25) Packaging space

The invention claimed is:

1. A packaging comprising resiliently expandable packaging for small-part items in the medical field, the packaging comprising:

a packaging body open on one side with a packaging space, closed at a bottom, which merges into a resiliently expandable closure part on its upper side, wherein a transition region between the closure part and the packaging space comprises one or more opposed locking knobs arranged therein, which form a resiliently expandable closure gap therebetween, wherein at least two opposing gripping ribs are arranged on the closure part and are arranged opposite one another on narrow sides of the packaging body, which are resiliently deformable in a direction directed towards one another.

2. The packaging according to claim 1, wherein the packaging body is designed as a resiliently expandable, flat, pocket-shaped packaging body.

3. The packaging according to claim 1, wherein the upper closure part is resiliently expandable by finger force.

4. The packaging of claim 1, wherein the at least two opposing gripping ribs are configured to form an open closure gap when suitable deformation is applied in a direction directed towards one another.

5. The packaging according to claim 1, wherein the locking knobs for forming the closure gap are arranged in the space between the opposing gripping ribs.

6. The packaging according to claim 1, wherein the packaging space is approximately bag-shaped for accommodating a plurality of items.

7. The packaging according to claim 1, wherein the locking knobs are arranged individually or in pairs on inner sides of a front wall and a rear wall.

8. The packaging according to claim 7, wherein the locking knobs are flush with one another and form a straight closure gap.

9. The packaging according to claim 7, wherein the locking knobs are offset from one another and form a labyrinth-like closure gap.

10. The packaging according to claim 1, wherein the locking knobs are arranged individually or in pairs only on an inner side of a front wall or an inner side of a rear wall.

11. The packaging according to claim 1, wherein the transition from the packaging space into a neck region of the closure part adjoining at the top is effected via an arched convex contour, so that the neck region is reduced in width in cross section compared to the packaging space.

12. The packaging according to claim 11, wherein the neck region forms an upper, undeformed oval opening which is defined by a peripheral edge and in that the opening is resiliently expandable.

13. The packaging according to claim 12, wherein the upper undeformed oval opening of the neck region can be closed by welding or gluing or sealing.

14. The packaging according to claim 1, wherein the packaging body is manufactured in one piece using a blow molding process and consists of a resilient plastics material, preferably a TPU plastics material.

15. The packaging according to claim 1, wherein the packaging consists of a plastics material with a hardness in the range of 45 to 95 shore-A and particularly preferably has a hardness of 85 shore-A+−5.

16. A resiliently expandable packaging system for small-part items in the medical field, the system comprising:

a packaging body open on a top side and closed at a bottom, the packaging body forming packaging space;

the open top side having a resiliently expandable closure part extending from the top side to the packaging space, wherein a transition region between the resiliently expandable closure part and the packaging space comprises one or more opposed locking knobs arranged therein, the locking knobs forming a resiliently expandable closure gap between the open top side and the packaging space, and wherein at least two opposing gripping ribs are arranged on the closure part and are arranged opposite one another on narrow sides of the packaging body, which are resiliently deformable in a direction directed towards one another.

* * * * *